United States Patent
Nakajima et al.

(10) Patent No.: US 7,398,687 B2
(45) Date of Patent: Jul. 15, 2008

(54) ULTRASONIC SENSOR

(75) Inventors: Akira Nakajima, Okazaki (JP);
Yasuhiro Kawashima, Okazaki (JP);
Hiroyuki Kani, Okazaki (JP); Tadao Shimizu, Chita (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 11/715,395

(22) Filed: Mar. 8, 2007

(65) Prior Publication Data
US 2007/0220981 A1 Sep. 27, 2007

(30) Foreign Application Priority Data
Mar. 23, 2006 (JP) .............................. 2006-080683
Jan. 15, 2007 (JP) .............................. 2007-005950

(51) Int. Cl.
*G01N 9/18* (2006.01)
*B60Q 1/00* (2006.01)

(52) U.S. Cl. .......................... 73/661; 73/632; 73/866.5; 340/435

(58) Field of Classification Search .................... 73/661, 73/632, 649, 596–600, 625; 340/435, 693.9
See application file for complete search history.

(56) References Cited

U.S. PATENT DOCUMENTS

| 6,759,950 | B2 | 7/2004 | Nishimoto et al. | |
| 7,240,555 | B2 * | 7/2007 | Kawashima | 73/632 |
| 7,278,314 | B2 * | 10/2007 | Sato et al. | 73/602 |
| 7,313,960 | B2 * | 1/2008 | Kawashima | 73/632 |
| 7,317,663 | B2 * | 1/2008 | Kawashima et al. | 367/188 |
| 2006/0021440 | A1 | 2/2006 | Kawashima | |
| 2006/0241474 | A1 * | 10/2006 | Kawashima et al. | 600/459 |
| 2006/0284515 | A1 * | 12/2006 | Nakajima | 310/311 |
| 2007/0062292 | A1 * | 3/2007 | Sato et al. | 73/649 |
| 2007/0230273 | A1 * | 10/2007 | Nakajima et al. | 367/140 |
| 2007/0230274 | A1 * | 10/2007 | Nakajima et al. | 367/140 |

FOREIGN PATENT DOCUMENTS

JP    2004-253912    9/2004

\* cited by examiner

*Primary Examiner*—Hezron E. Williams
*Assistant Examiner*—Jacques M. Saint-Surin
(74) *Attorney, Agent, or Firm*—Nixon & Vanderhye PC (57) ABSTRACT

A cover member of an ultrasonic sensor has a first engagement portion and a second engagement portion, which are respectively engaged with a third engagement portion and a fourth engagement portion of a sensor body. The engagement portions are arranged in such a manner that a force applied to the cover member due to an engagement between the first engagement portion and the third engagement portion and a force applied to the cover member due to an engagement between the second engagement portion and the fourth engagement portion respectively have opposite directions to be substantially countervailed when the sensor body is attached to the cover member. Thus, the cover member can be restricted from slanting when the sensor body is fixed to the cover member.

6 Claims, 10 Drawing Sheets

ULTRASONIC SENSOR

CROSS REFERENCE TO RELATED APPLICATION

This application is based on a Japanese Patent Application No. 2006-80683 filed on Mar. 23, 2006 and a Japanese Patent Application No. 2007-5950 filed on Jan. 15, 2007, the disclosure of which is incorporated herein by reference.

FIELD OF THE INVENTION

The present invention relates to an ultrasonic sensor.

BACKGROUND OF THE INVENTION

Generally, an ultrasonic sensor is provided with a sensor body, which has an ultrasonic transducer and is attached to a bumper of a vehicle. The ultrasonic transducer generates ultrasonic wave. By receiving reflection wave of the ultrasonic wave, an obstacle near the bumper is detected.

Figure 12:
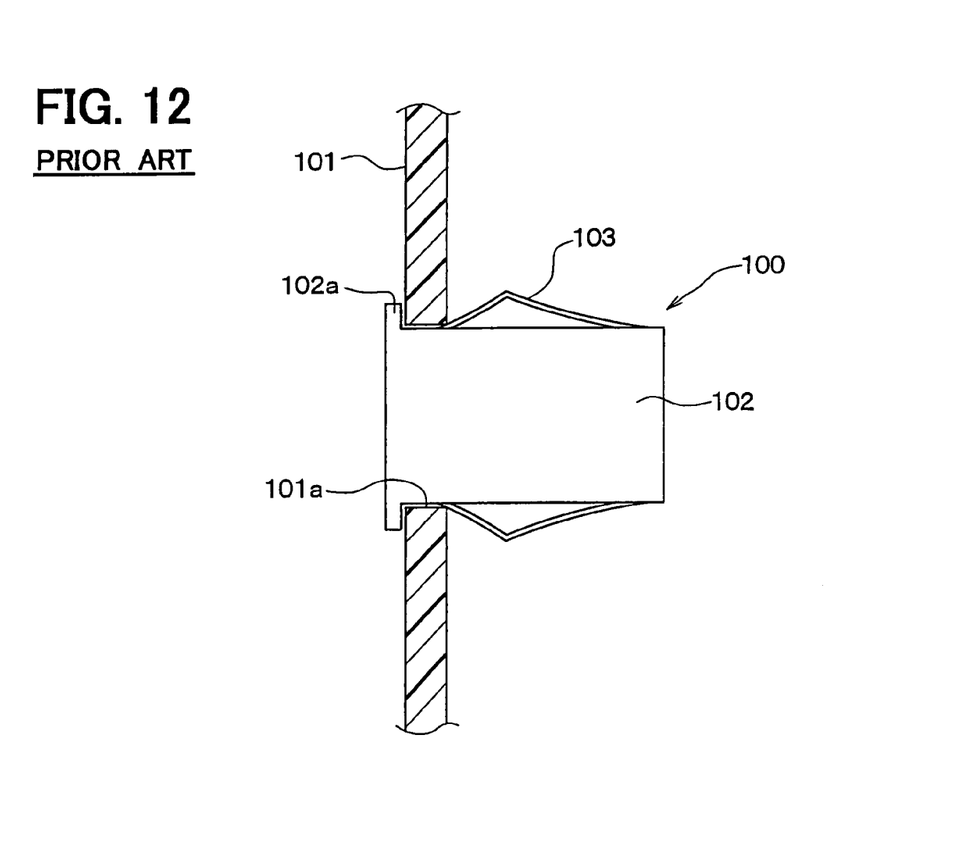
FIG. 12 is a partially sectional view showing a fixing construction of an ultrasonic sensor to a bumper according to a prior art.

For example, with reference to JP-2003-9270A (U.S. Pat. No. 6,759,950), FIG. 12 is a partially sectional view showing a mounting construction for fixing a conventional ultrasonic sensor 100 to a bumper 101. As shown in FIG. 12, a sensor body 102 of the ultrasonic sensor 100 has a circular column shape. By inserting the sensor body 102 in a circular hole 101a arranged at the bumper 101 from the outside of the bumper 101, the sensor body 102 is fixed to the bumper 101.

Specifically, the sensor body 102 has a flange 102a which is positioned at the rear end thereof in the insertion direction of the sensor body 102 to the bumper 101. A V-shaped metal spring 103 is provided around the outer periphery of the sensor body 102.

Thus, when the sensor body 102 is inserted through the hole 101a of the bumper 101, the expanding force in the diameter direction of the sensor body 102 generated by the metal spring 103 is applied to the wall face constructing the hole 101a of the bumper 101, in such a state that movement in the insertion direction of the sensor body 102 is regulated by the flange 102a. Thus, the sensor body 102 is substantially fixed to the bumper 101.

In recent years, the ultrasonic sensor is becoming intelligent, and a circuit board on which not only the ultrasonic transducer but also a signal processing circuit and the like are arranged is being housed in the sensor body. Thus, the sensor body is enlarged, and there occurs a problem that the sensor body cannot be inserted through the hole of the bumper from the outside of the bumper. Therefore, it is necessary to fix the ultrasonic sensor to the bumper by a structure different from the conventional structure.

In order to solve the above-described problem, the following construction is considered by the inventors of the present invention. That is, with reference to FIG. 13, a bezel 4 (cover) which has a cylindrical shape and has a flange 4a at one end thereof is provided. The bezel 4 is inserted from the outside of a bumper 2 into a hole 2a of the bumper 2, to be fixed to the bumper 2. Thereafter, a circular column portion in which an ultrasonic transducer of the sensor body 3 is disposed is inserted in a hollow portion of the bezel 4 from the inside of the bumper (that is, in direction opposite to insertion direction of bezel 4 to hole 2a of bumper 2), so that the sensor body 3 is fixed to the bumper 2 via the bezel 4.

Figure 13:
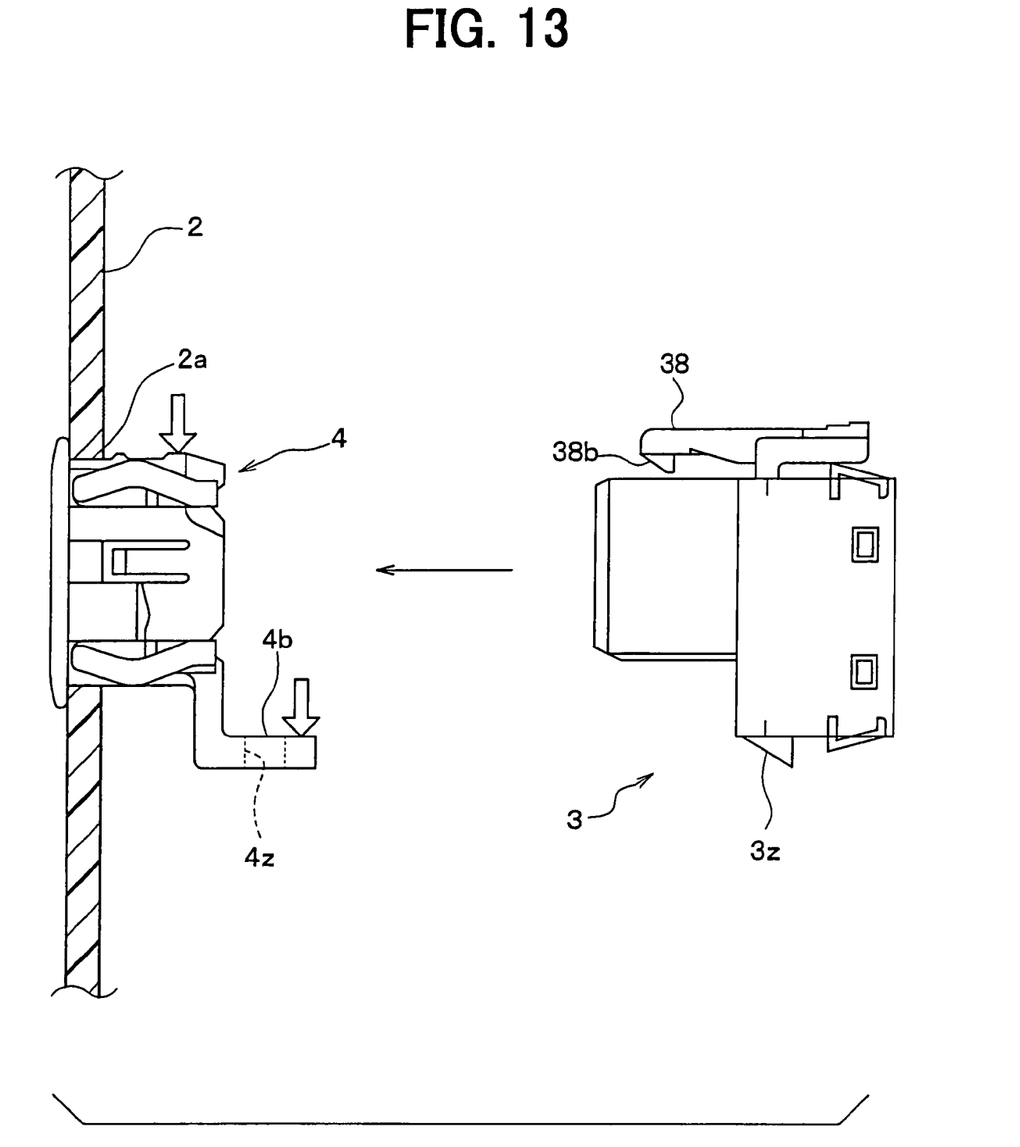
FIG. 13 is a schematic view showing attachment of an ultrasonic sensor according to a comparison example proposed by the inventors of the present invention.

In this case, because it is necessary to hold the sensor body 3 having a large size at the bezel 4 which functions as a fixing member, the bezel 4 is to be firmly fixed to the bumper 2 and the sensor body 3 is to be firmly fixed to the cover member 4.

Therefore, as shown in FIG. 13, it is proposed by the inventors of the present invention to provide a snap fit 4b, a nail portion 3z, a lance 38 and a hole portion (not shown) which is engaged with a nail portion 38b of the lance 38 and positioned at the upper side (with respect to up-down direction of drawing of FIG. 13) of the bezel 4. In this case, the snap fit 4b has a hole portion (not shown) positioned at the lower side (with respect to up-down direction of drawing of FIG. 13) of the bezel 4. The nail portion 3z is engaged with a hole portion 4z of the snap fit 4b, and positioned at the lower side of the sensor body 3. The lance 38 which is provided with the nail portion 38b is positioned at the upper side of the sensor body 3.

In this case, when the sensor body 3 is fixed to the bezel 4, the nail portion 38b of the lance 38 contacts the outer surface of the side wall of the bezel 4 so that the lance 38 is elastically deformed. When the nail portion 38b of the lance 38 comes to the hole portion of the bezel 4, the shape of the lance 38 recovers so that the nail portion 38b enters into the hole portion. Thus, the nail portion 38b is engaged with the hole portion.

Similarly, the snap fit 4b is pressed by the nail portion 3z of the sensor body 3 to be elastically deformed. When the hole portion 4z of the snap fit 4b comes to the nail portion 3z, the shape of the snap fit 4b recovers so that the nail portion 3z enters the hole portion 4z. Thus, the nail portion 3z and the hole portion 4z are engaged with each other. Thus, the bezel 4 and the sensor body 3 can be further firmly fixed via the lance 38, the snap fit 4b and the like.

However, in the above-described construction, as indicated by the arrow in FIG. 13, an elastic reaction force of the lance 38 is applied to the bezel 4 in a direction facing the lower side, and a force pressing the snap fit 4b by the nail portion 3z is applied in a direction facing the lower side. Therefore, the two forces are applied to the bezel 4 in the same direction. Thus, the cover member 4 is susceptibly slanted.

Similarly, there also occurs the problem in the case where the ultrasonic sensor is mounted to a vehicle component other than the bumper.

SUMMARY OF THE INVENTION

In view of the above-described disadvantages, it is an object of the present invention to provide an ultrasonic sensor where a cover member thereof is restricted from slanting, when a senor body thereof is mounted through the cover member.

According to the present invention, an ultrasonic sensor includes a cover member having a hollow portion which has an opening at one end thereof, and a sensor body having an ultrasonic transducer. A part of the sensor body which includes the ultrasonic transducer is inserted in the hollow portion from the opening of the cover member. The part of the sensor body is inserted in the hollow portion of the cover member from one side of a base after the cover member is inserted through a hole portion of the base from the other side of the base, so that the sensor body is attached to the base through the cover member. The one side and the other side of the cover member are opposite to each other. The cover member has a first engagement portion and a second engagement portion which are positioned to be opposite to each other with respect to the hollow portion of the cover member. The sensor body has a third engagement portion which is engaged with the first engagement portion, and a fourth engagement portion which is engaged with the second engagement portion. The first engagement portion, the second engagement portion, the third engagement portion and the fourth engagement portion are arranged, in such a manner that a force applied to the cover member due to an engagement between the first engagement portion and the third engagement portion and a force applied to the cover member due to an engagement between the second engagement portion and the fourth engagement portion respectively have directions opposite to each other when the sensor body is attached to the cover member.

Thus, the forces generated by the engagement portions are applied to the cover member 4 respectively in the opposite directions to be substantially countervailed, when the sensor body 3 is fixed with respect to the cover member 4. Therefore, the cover member 4 can be restricted from slanting when the sensor body 3 is fixed to the cover member 4.

BRIEF DESCRIPTION OF THE DRAWINGS

Other objects, features and advantages of the present invention will become more apparent from the following detailed description made with reference to the accompanying drawings, in which.

DETAILED DESCRIPTION OF THE EXAMPLED EMBODIMENTS

Preferred Embodiment

Figure 1:
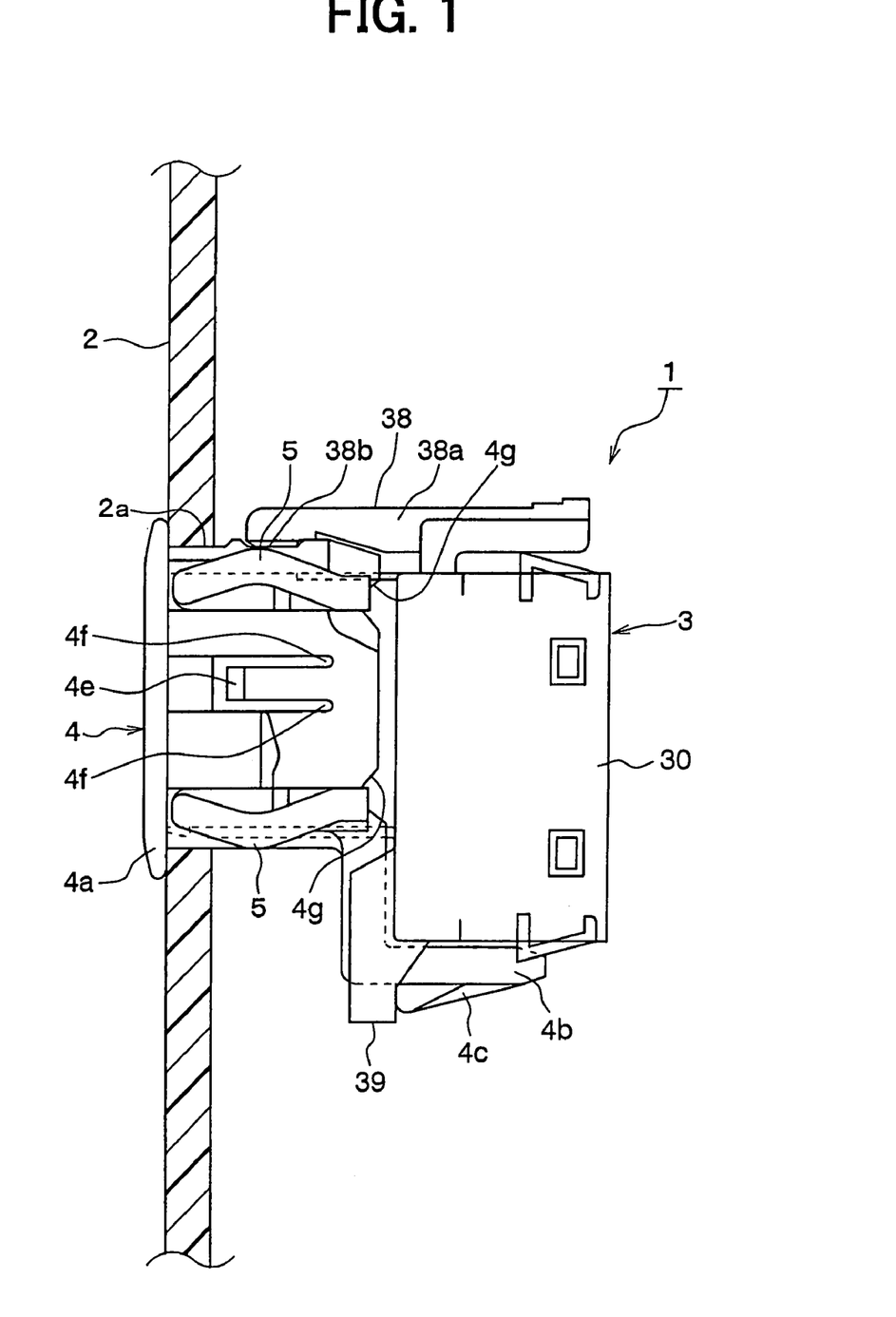
FIG. 1 is a partially sectional side view showing an ultrasonic sensor which is attached to a bumper according to a preferred embodiment of the present disclosure.

An ultrasonic sensor 1 according to a preferred embodiment of the present invention will be described with reference to FIGS. 1-11. With reference to FIG. 1, the ultrasonic sensor 1 can be suitably mounted to a base, for example, a bumper 2 of a vehicle to be used as a back sonar or a corner sonar or the like.

The ultrasonic sensor 1 has a sensor body 3 and a cover member 4 (bezel), and can be fixed at a hole portion 2a of the bumper 2, for example. The cover member 4 has a hollow portion which has an opening at one end thereof. The cover member 4 of the ultrasonic sensor 1 is inserted through the hole portion 2a from the outer side (left side in FIG. 1) of the bumper 2, and then the sensor body 3 is inserted into the hollow portion of the cover member 4 from the inner side (right side in FIG. 1) of the bumper 2. Thus, the ultrasonic sensor 1 is fixed to the bumper 2.

Figure 2A:
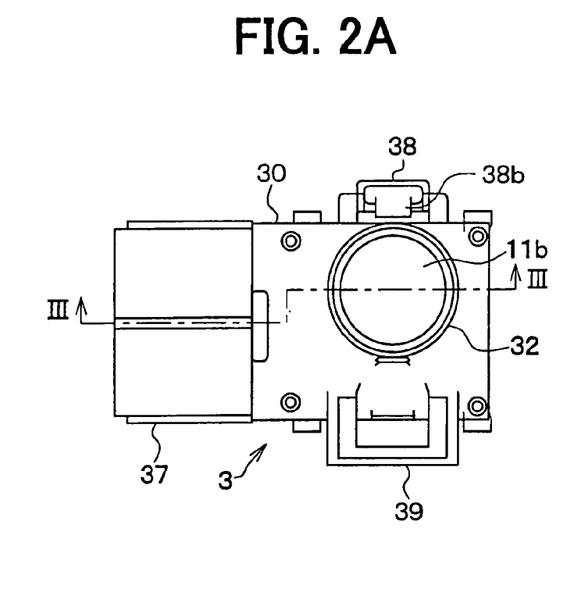
FIG. 2A is a front view showing the ultrasonic sensor according to the preferred embodiment.
Figure 2B:
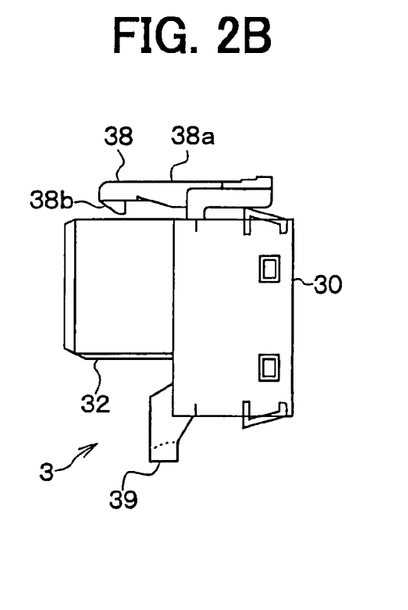
FIG. 2B is a right side view showing the ultrasonic sensor.
Figure 2C:
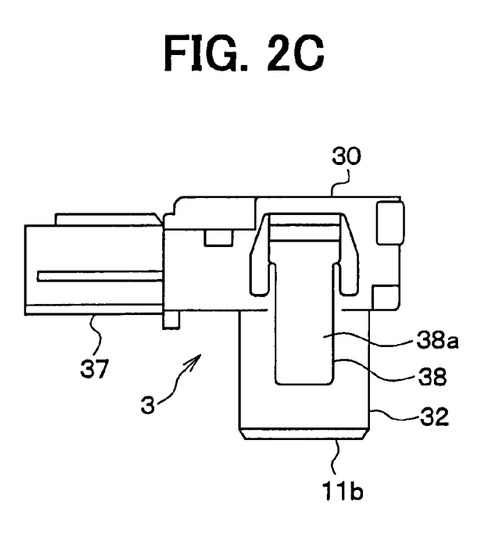
FIG. 2C is a plan view showing the ultrasonic sensor.
Figure 2D:
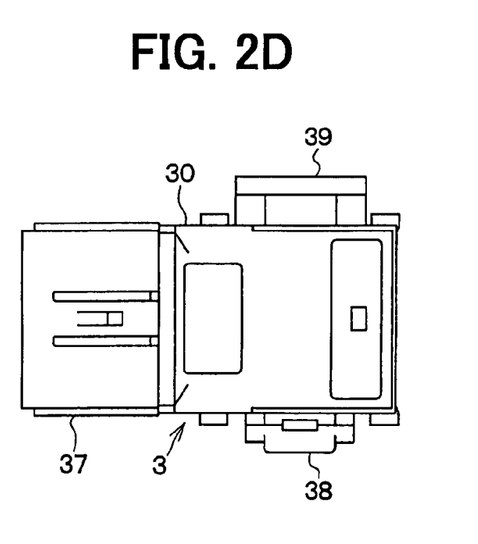
FIG. 2D is a rear view showing the ultrasonic sensor.
Figure 3:
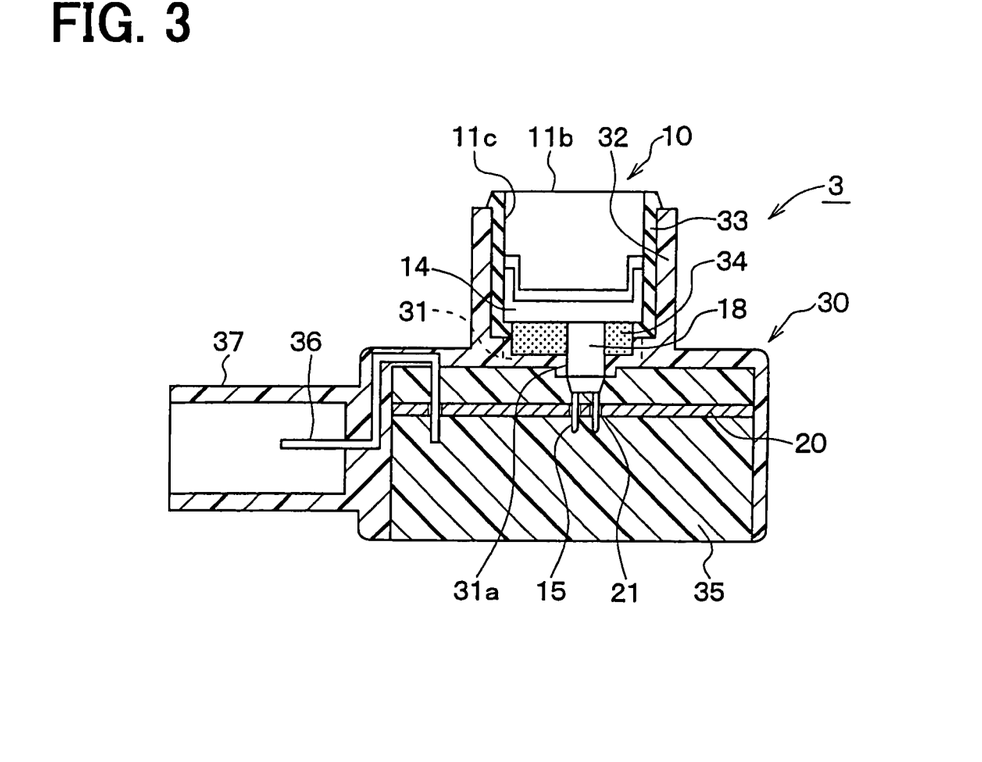
FIG. 3 is a cross-sectional view taken along a line III-III in FIG. 2A.
Figure 4:
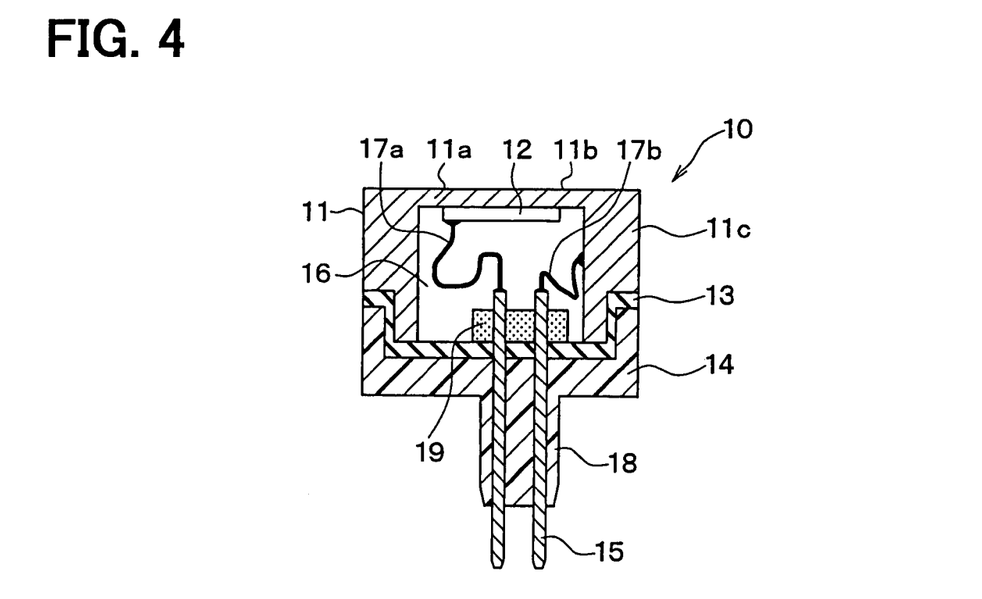
FIG. 4 is a cross-sectional view showing an ultrasonic transducer according to the preferred embodiment.

As shown in FIGS. 2A-2D and 3, the sensor body 3 includes an ultrasonic transducer 10 (microphone), a circuit board 20 and a case 30, in which the ultrasonic transducer 10 and the circuit board 20 are integrally housed. With reference to FIG. 4, the ultrasonic sensor 10 has a housing 11, a piezoelectric element 12, a spacer 13, a base member 14, and a pair of connection pins 15.

The housing 11 is made of a conductive material, for example, a metal material or an insulating material having a surface at which a conductive film is arranged. The housing 11 which can have a bottomed cylindrical shape has therein an internal space 16. The piezoelectric element 12 is arranged in the internal space 16, and adhered to the inner surface of a bottom 11a of the housing 11. The outer surface of the bottom 11a serves as a vibration surface 11b. In this embodiment, aluminum can be used as the conductive material. The vibration surface 11b can have a circular shape, for example.

The piezoelectric element 12 can be made of a piezoelectric ceramics (for example, lead zirconate titanate), and is provided with electrodes (not shown) at a facade surface and a back surface thereof.

One of the electrodes of the piezoelectric element 12 is electrically connected to one of the pair of connection pins 15 via a lead 17a. The other of the electrodes of the piezoelectric element 12 is adhered to the bottom 11a of the housing 11 by, for example, a conductive adhesive. The other of the electrodes of the piezoelectric element 12 is connected to a lead 17b via the housing 11 made of the conductive material, and electrically connected to the other connection pin 15.

The internal space 16 of the housing 11 is filled with felt, silicon or the like, so that unnecessary vibrations transmitted from the vibration surface to the connection pins 15 are suppressed.

The spacer 13 is arranged at an opening end of the housing 11, and disposed between the opening end of the housing 11 and the base member 14. The spacer 13 is an elastic member for suppressing transmission of the unnecessary vibrations generated at a cylindrical portion 11c (between bottom 11a and opening end of housing 11) of the housing 11 in association with vibrations of the bottom 11a of the housing 11 to the base member 14 (to which connection pins 15 are fixed). The spacer 13 can be made of, for example, a silicon rubber. Alternatively, the spacer 13 can be also omitted.

The base member 14 is attached to the surface of the spacer 13 to be fixed to the housing 11. This surface and the opening end of the housing 11 are respectively arranged at two opposite sides of the spacer 13. The base member 14 can be made of an insulating material such as a synthetic resin (for example, ABS resin).

The base member 14 has a protection portion 18 for covering the connection pins 15. The protection portion 18 projects outwards from the base member 14 to the side of the circuit board 20. The connection pins 15 are disposed to penetrate the protection portion 18. By insert-molding the connection pins 15 when the base member 14 is constructed, a part of the connection pins 15 is buried and fixed in the base member 14.

The connection pin 15 is made of a conductive material having a main ingredient such as copper. The connection pin 15 can be constructed by a rod member having a thickness of, for example, 0.5 mmϕ (i.e., having diameter of 0.5 mm).

Furthermore, the ultrasonic transducer 10 has a foam elastic member 19 made of, for example, foam silicon. The foam elastic member 19 is provided to restrict transmission of vibration to the base member 14, and the connection pins 15 are disposed to penetrate the foam elastic member 19.

The housing 11, the spacer 13, the base member 14, and the foam elastic member 19 are integrated to each other, for example, by bonding through adhesive such as silicon adhesive. Thus, the ultrasonic transducer 10 is constructed.

The ultrasonic transducer 10 (which is constructed as described above) and the circuit board 20 are arranged in the case 30 which is made of synthetic resin or the like. Thus, the ultrasonic sensor 1 is constructed.

The case 30 can have a hollow rectangular-parallelepiped shape, for example. The case 30 has a guide portion 31 for positioning the connection pines 15 with respect to a connection position of the circuit board 20. The guide portion 31 (having plate shape, for example) partitions the internal space of the case 30 into a space in which the ultrasonic transducer 10 is disposed and a space in which the circuit board 20 is disposed. The guide portion 31 has a positioning hole 31a through which the connection pins 15 and the protection portion 18 are inserted.

As shown in FIG. 3, the case 30 has an opening portion 32 for housing the ultrasonic transducer 10. The opening portion 32 can be a cylindrical projection portion with respect to the part of the case 30 in which the circuit board 20 is housed.

The ultrasonic transducer 10 is inserted in the open portion 32, in such a manner that the outer surface of the ultrasonic transducer 10 is covered by a cylindrical elastic member 33 and a foam elastic member 34 (as elastic member for suppressing vibration) is arranged between the base member 14 of the ultrasonic sensor 10 and the guide portion 31. Thus, the ultrasonic transducer 10 is attached to the case 30.

In a state where the ultrasonic transducer 10 is assembled in the case 30, the connection pins 15 are inserted in the positioning hole 31a of the guide portion 31, and the tip portions of the connection pins 15 are inserted through holes 21 arranged at the circuit board 20. The electrical connection between the tip portions of the connection pins 15 and the through holes 21 can be provided by soldering or the like.

The vibration surface 11b of the ultrasonic transducer 10 is exposed from the open portion 32 of the case 30, so that ultrasonic waves generated by the ultrasonic transducer 10 can be transmitted to the outside of the case 30.

The foam elastic member 34 is arranged between an outer surface of an end of the base member 14 and the guide portion 31. The foam elastic member 34 is provided with a notch, through which the protection portion 18 is inserted.

Similarly to the foam elastic member 19 which is arranged in the housing 11 of the ultrasonic transducer 10, the foam elastic member 34 is made of silicon foam, and the connection pins 15 and the protection portion 18 are disposed to penetrate the foam elastic member 34.

The elastic member 33 can be made of a silicon rubber or the like, to suppress transmission of unnecessary vibration from the ultrasonic transducer 10 to the case 30. In this case, the ultrasonic transducer 10 and the foam elastic member 34 are housed in the opening portion 32 of the case 30, with the elastic member 33 being sandwiched between the inner surface of the opening portion 32 and the circumferential-direction outer surfaces of the ultrasonic transducer 10 and the foam elastic member 34.

The ultrasonic transducer 10 (with base member 14), the elastic member 33, and the foam elastic member 34 can be fixedly bonded to each other by a silicone adhesive, for example.

The space in the case 30 which is partitioned by the guide portion 31 and in which the circuit board 20 is arranged is filled with a moisture-proof member 35. The moisture-proof member 35 can be constructed of, for example, a silicone resin or a urethane resin. In this embodiment, a silicone resin is applied.

As shown in FIG. 3, an external output terminal 36 for outputting from the circuit board 20 to the external is provided. One end side of the external output terminal 36 is exposed from a connector 37 which protrudes outwards from an outer surface of the case 30.

Furthermore, as shown in FIGS. 2A to 2D, the case 30 is provided with a lance 38 and a receiving portion 39 which protrudes from the outer surface of the case 30 and are respectively arranged at two opposite sides of the case 30. For example, the lance 38 can be provided at the top surface (i.e., surface of upper side of drawing of FIG. 2A) of the case 30. The receiving portion 39 can be provided at the bottom surface (i.e., surface of lower side of drawing in FIG. 2A) of the case 30.

The lance 38 for fixing the sensor body 3 to the cover member 4 is a nail-shaped engagement portion which projects from the top surface of the case 30 in the same direction as the protrusion direction of the open portion 32 from the case 30.

The lance 38 has a rod portion 38a and a nail portion 38b. The rod portion 38a projects from the top surface of the case 30 in the same direction as that of the open portion 32 from the case 30. The nail portion 38b is arranged at the tip of the rod portion 38a, and positioned at the side of the open portion 32. In this case, the nail portion 38b protrudes from the tip of the rod portion 38a toward the side of the open portion 32.

The receiving portion 39 for fixing the sensor body 3 to the cover member 4 is a frame-shaped retaining part which projects downward from the bottom surface of the case 30. For example, as shown in FIGS. 2A and 2D, the receiving portion 39 can have a square frame shape when viewed from the projection direction of the open portion 32 from the case 30. A snap fit 4b arranged at the cover member 4 which will be described later can be inserted in the hole of the receiving portion 39.

The part of the sensor body 3 where the ultrasonic transducer 10 and the open portion 32 of the case 30 are arranged, that is, the projection portion of the case 30 constructs an insertion portion to be inserted in the hollow portion of the cover member 4. Therefore, the projection direction of the open portion 32 from the case 30 corresponds to the insertion direction of the sensor body 3 to the cover member 4.

FIGS. 5A, 5B, 5C, 5D, and 5E are respectively a front view, a left side view, a rear view, a plan view, and a bottom view of the cover member 4. FIG. 6 is a partially enlarged sectional view of the cover member 4, taken along a line VI-VI in FIG. 5C.

The cover member 4 can be made of a resin, for example. The cover member 4 has the hollow portion (having substantially cylindrical shape, for example) and a flange 4a, which has a diameter larger than an outer diameter of the hollow portion and is arranged at one end of the hollow portion. The hollow portion of the cover member 4 defines therein a space which can have a shape and a size corresponding to those of the outer surface of the open portion 32 of the case 30 of the sensor body 3. The open portion 32 and the ultrasonic transducer 10 are inserted in the hollow portion of the cover member 4.

Figure 5A:
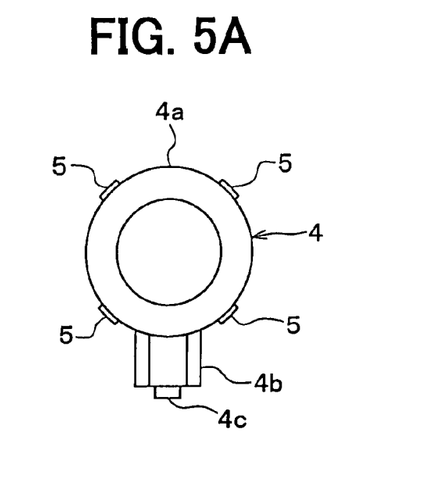
FIG. 5A is a front view showing a cover member according to the preferred embodiment.
Figure 5B:
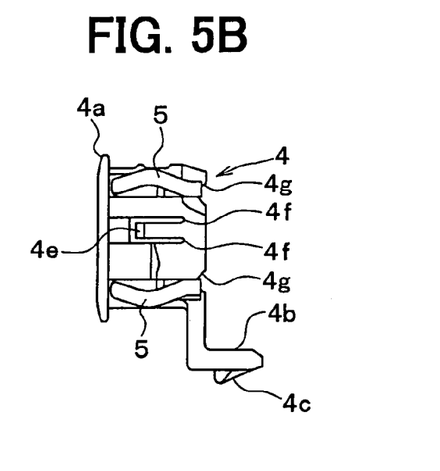
FIG. 5B is a left side view showing the cover member.
Figure 6:
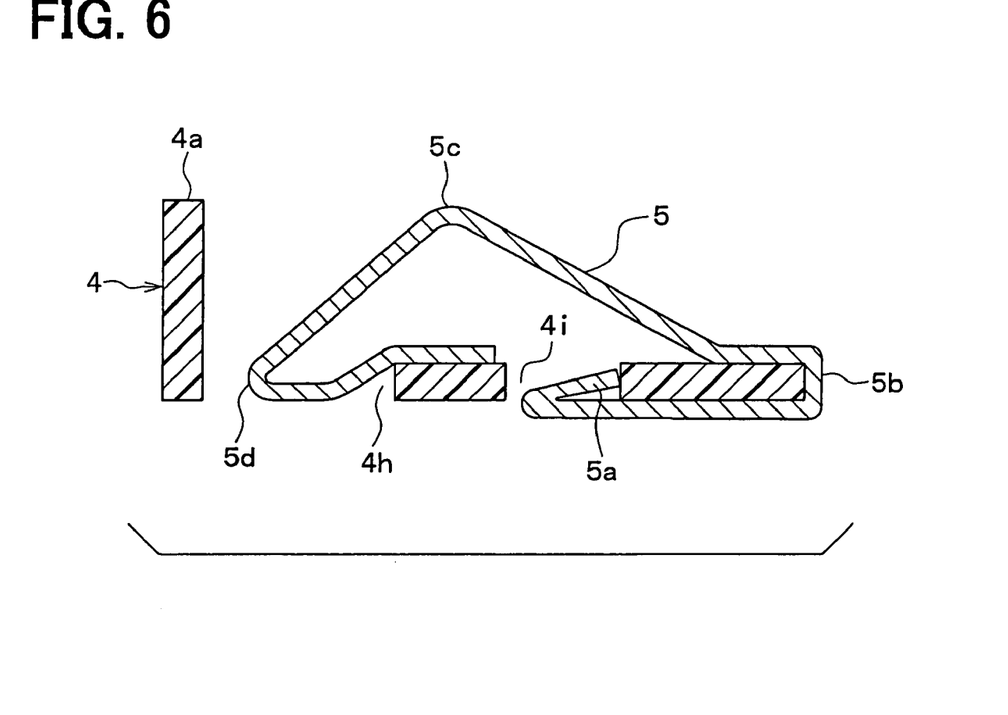
FIG. 6 is a partially enlarged sectional view taken along a line VI-VI in FIG. 5C.

With reference to FIG. 5B, the snap fit 4b protrudes from the outer surface of the hollow portion of the cover member 4, and is arranged at the lower side of the outer surface, for example. The snap fit 4b functions as a nail-shaped engagement portion. A nail portion 4c is arranged at the tip of the snap fit 4b, and protrudes outward therefrom. As shown in FIG. 1, by inserting the nail portion 4c into the hole of the receiving portion 39 of the case 30, the nail portion 4c is retained by the receiving portion 39. Thus, the cover member 4 and the sensor body 3 are fixed more firmly.

Figure 5C:
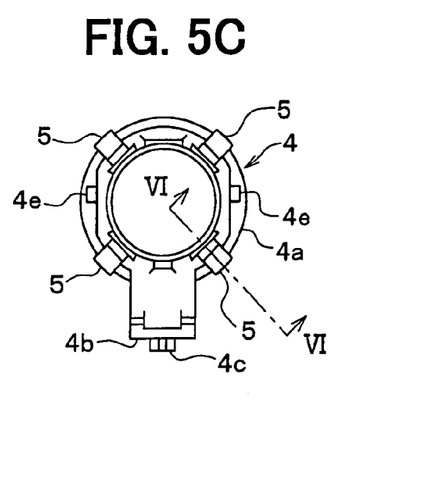
FIG. 5C is a rear view showing the cover member.
Figure 5D:
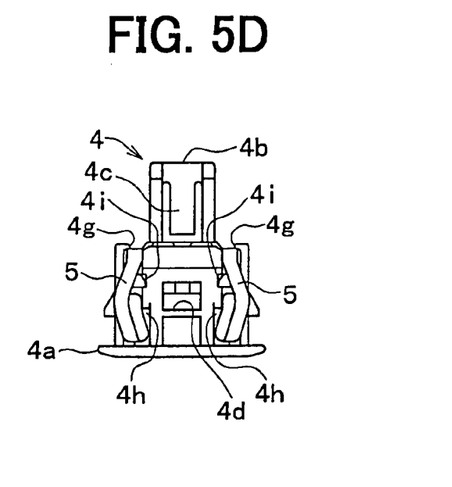
FIG. 5D is a plan view showing the cover member.
Figure 5E:
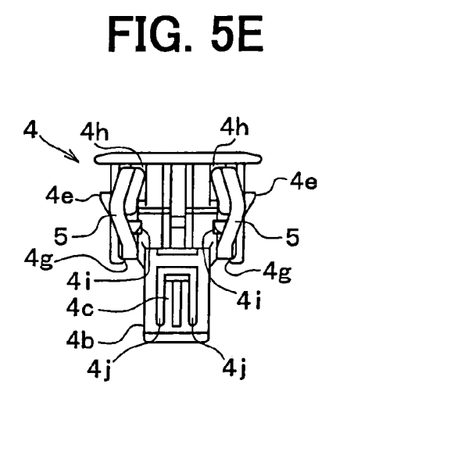
FIG. 5E is a bottom view showing the cover member.

As shown in FIG. 5E, the snap fit 4b is provided with a slit 4j which has a ⊐-like shape to surround the nail portion 4c, so that the nail portion 4c is susceptible to elastic deformation. The slit 4j surrounds the two opposite sides (along protrusion direction of snap fit 4b from hollow portion of cover member 4) of the nail portion 4c, and the rear end side (i.e., side of hollow portion of cover member 4) of the nail portion 4c.

That is, the slit 4j is arranged at the rear side of the nail portion 4c with respect to the insertion direction of the nail portion 4c into the hole of the receiving portion 39 of the sensor body 3. When the tip portion of the snap fit 4b is inserted into the hole of the receiving portion 39, the nail portion 4c is bent (due to elastic deformation) with a front side thereof in this insertion direction as a fulcrum, to be readily inserted into the hole.

Figure 10:
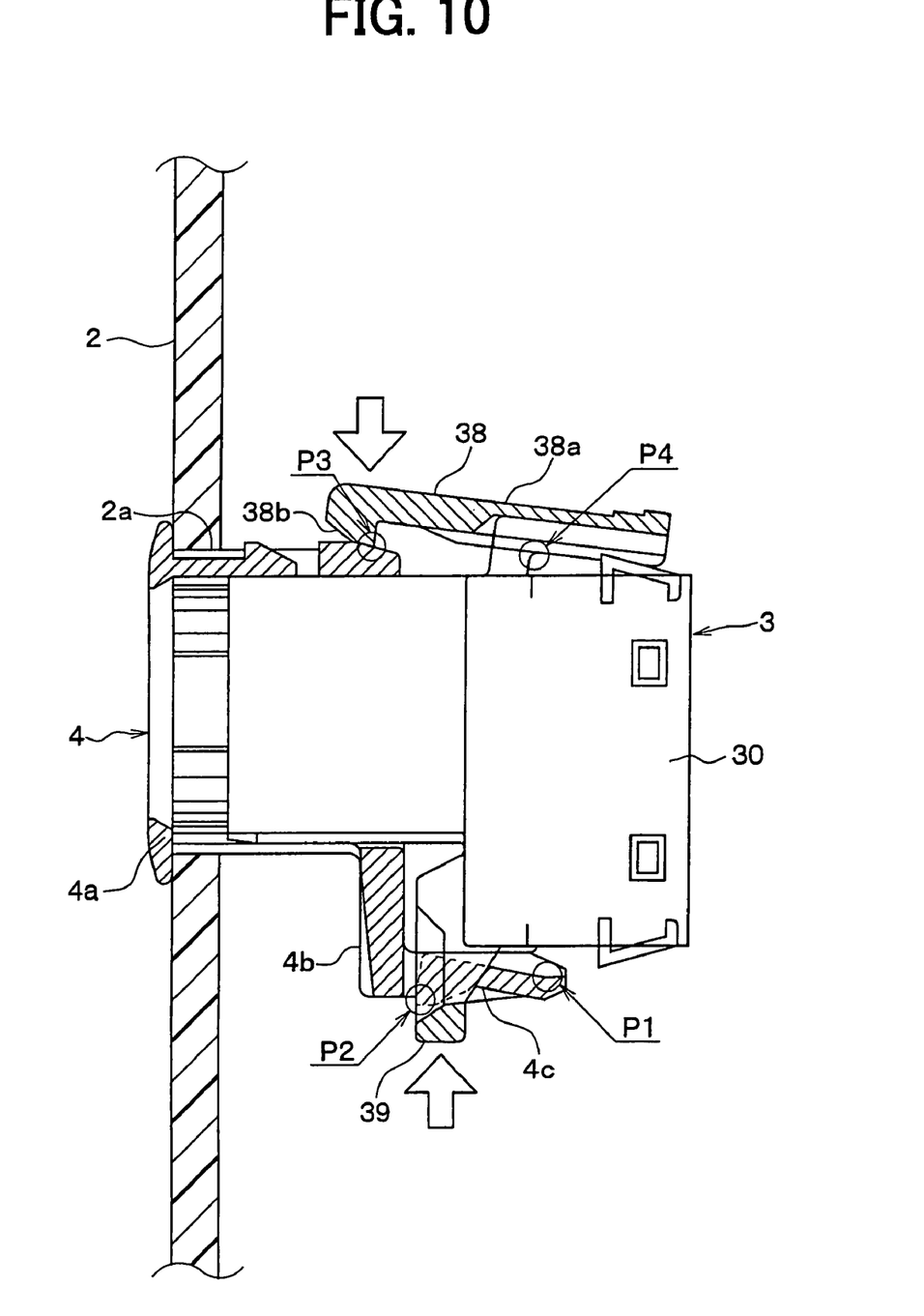
FIG. 10 is a partially enlarged sectional view showing a state when the ultrasonic transducer and an opening portion of a sensor body are inserted into a hollow portion of the cover member according to the preferred embodiment.

Thus, when the nail portion 4c returns to the original shape thereof after the tip portion of the snap fit 4b is inserted into the hole of the receiving portion 39, the wall surface of the tip portion of the snap fit 4b can almost contact the inner wall of the lance 38 with little gap, at the part of the tip portion of the snap fit 4b which is positioned at the rear side of the nail portion 4c, with reference to FIG. 10.

The cover member 4 has a hole portion 4d (engagement hole) which is arranged at the upper surface (at upper side of drawing of FIG. 1, FIG. 5B, for example) thereof and into which the nail portion 38b of the lance 38 provided at the case 30 is to be inserted. In this case, the hole portion 4d is arranged at the hollow portion of the cover member 4.

The engagement hole 4d has a substantial square shape when viewed from the facade side. As shown in FIG. 1, when the nail portion 38b of the lance 38 is inserted into the engagement hole 4d, the nail portion 38b is retained by the inner wall of the engagement hole 4d. Thus, the fixation of the sensor body 3 to the cover member 4 can become further firmly.

Detachment-restricting nails 4e are arranged at the outer surface of the hollow portion of the cover member 4, and respectively positioned at the left side and the right side (as shown in FIG. 5C) of the cover member 4. The detachment-restricting nail 4e is arranged at a position in consideration of the thickness of the bumper 2. In this case, the detachment-restricting nail 4e is spaced from the end surface of the flange 4a with a distance substantially equal to the thickness of the bumper 2 or slightly larger than this thickness. The detachment-restricting nail 4e is provided in order to prevent the cover member 4 from leaving from the bumper 2.

After the cover member 4 is attached to the bumper 2, a force is applied to the cover member 4 in the direction in which the cover member 4 leaves from the bumper 2 when the opening portion 32 of the case 30 of the sensor body 3 is inserted into the cover member 4. Therefore, when the cover member 4 is inserted into the bumper 2, the detachment-restricting nail 4e is retained by the end surface of the bumper 2 so that the cover member 4 can be restricted from leaving from the bumper 2.

As shown in FIG. 5B, a slit 4f is arranged to surround the two opposite sides of each of the detachment-restricting nail 4e. Thus, the rod-shaped portion of the detachment-restricting nail 4e surrounded by the slit 4f is susceptible to stress deformation, so that the detachment-restricting nail 4e can be restricted from hampering the insertion when the cover member 4 is inserted to the bumper 2.

Furthermore, multiple (e.g., four) grooves 4g are arranged at the cover member 4 to have a substantially equal distance from the central axis of the hollow portion of the cover member 4. As shown in FIG. 6, two through holes 4h and 4i are provided in each of the grooves 4g, and arranged substantially in the axial direction of the hollow portion of the cover member 4.

A metal spring 5 is arranged along each of the grooves 4g. A wall portion can be arranged between the through holes 4h and 4i, so that the spring force of the spring 5 can be heightened. That is, because the tip of the spring 5 contacts the wall portion of the through hole 4h, the spring 5 can be restricted from entering into the through hole 4h. Therefore, an elastic reaction force generated by the spring 5 can be heightened. Alternatively, the through hole 4h and 4i can be also constructed as a single through hole.

Specifically, the spring 5 can be constructed by a thin rod-shaped metal material by bending process or the like. The spring 5 has a nail portion 5a constructed of one end of the rod-shaped metal material which is bent to have a nail shape, a U-like portion 5b which is bent to have a U-like shape corresponding to the opening end shape of the hollow portion of the cover member 4, a convex portion 5c which protrudes from the outer surface of the hollow portion of the cover member 4 in the diameter direction of the hollow portion, and a loopback portion 5d which is constructed by bending the other end of the rod-shaped metal material back to the side of the nail portion 5a.

With reference to FIG. 6, when the nail portion 5a of the spring 5 is inserted from the opening end of the hollow portion of the cover member 4 until the U-like portion 5b contacts the opening end of the hollow portion of the cover member 4, the nail portion 5a enters into the through hole 4i to be retained by the end surface of the through hole 4i so that the spring 5 is fixed to the cover member 4. Therefore, the part of the spring 5 which is at the side fixed to the cover member 4, that is, the U-like portion 5b, constructs a fixation end, and the loopback portion 5d constructs a free end. Thus, the spring 5 can function as a spring.

That is, both the bumper 2 and the side surface of the opening portion 32 of the sensor body 3 contact the free end of the spring 5. The elastic force of the spring 5 is applied to the bumper 2 in an expanding direction thereof in a diameter direction of the cover member 4. The elastic force of the spring 5 is applied to the opening portion 32 of the sensor body 3 in a shrinking direction thereof in a diameter direction of the cover member 4.

According to this embodiment, the sensor body 3 is fixed to the bumper 2 through the cover member 4. In this case, the cover member 4 can be firmly fixed to the bumper 2, and the sensor body 3 can be firmly fixed to the cover member 4. Thus, the ultrasonic sensor 1 can be firmly fixed to the bumper 2.

Figure 7:
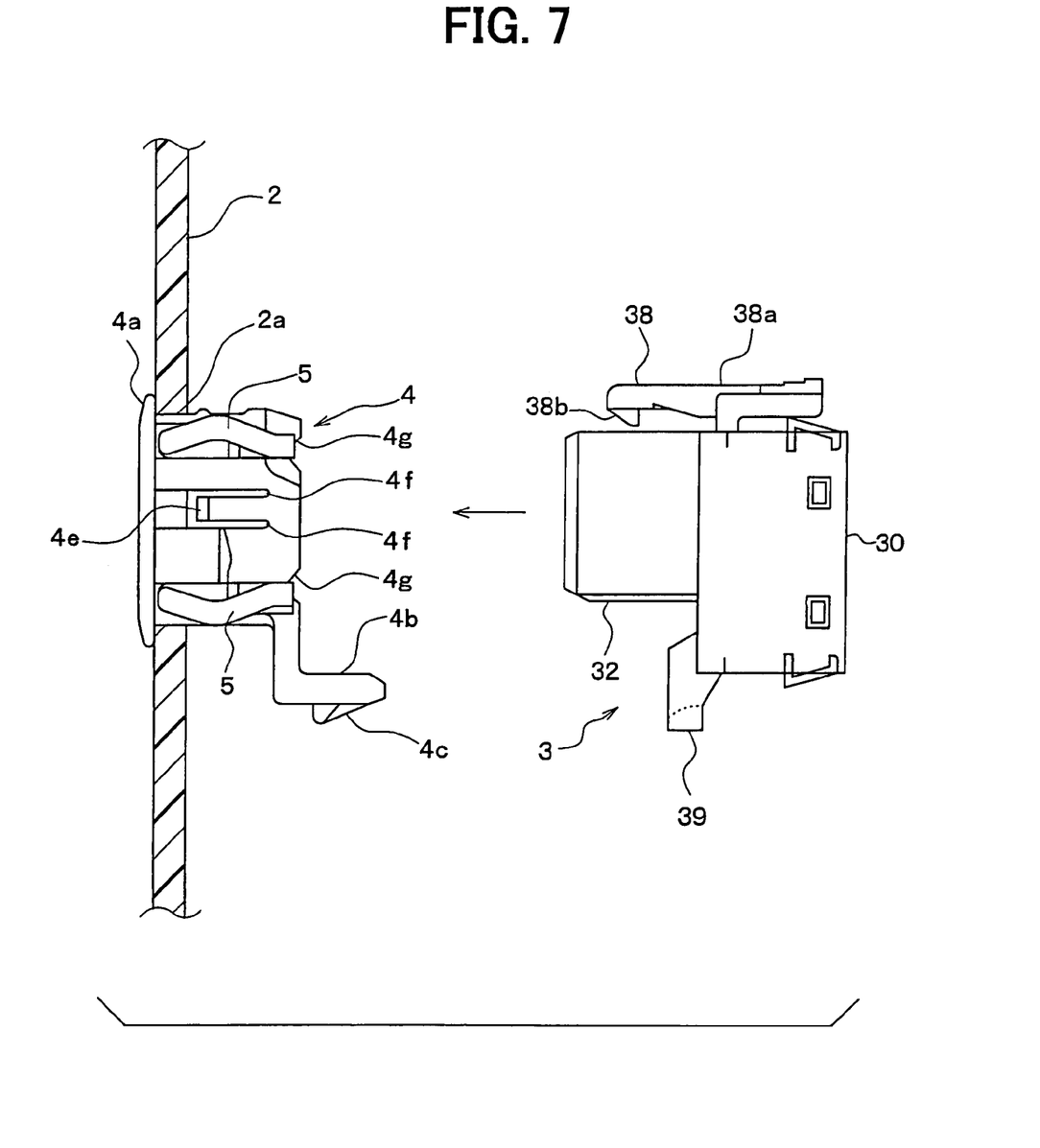
FIG. 7 is a schematic view showing the ultrasonic sensor before attachment to the bumper according to the preferred embodiment.
Figure 8:
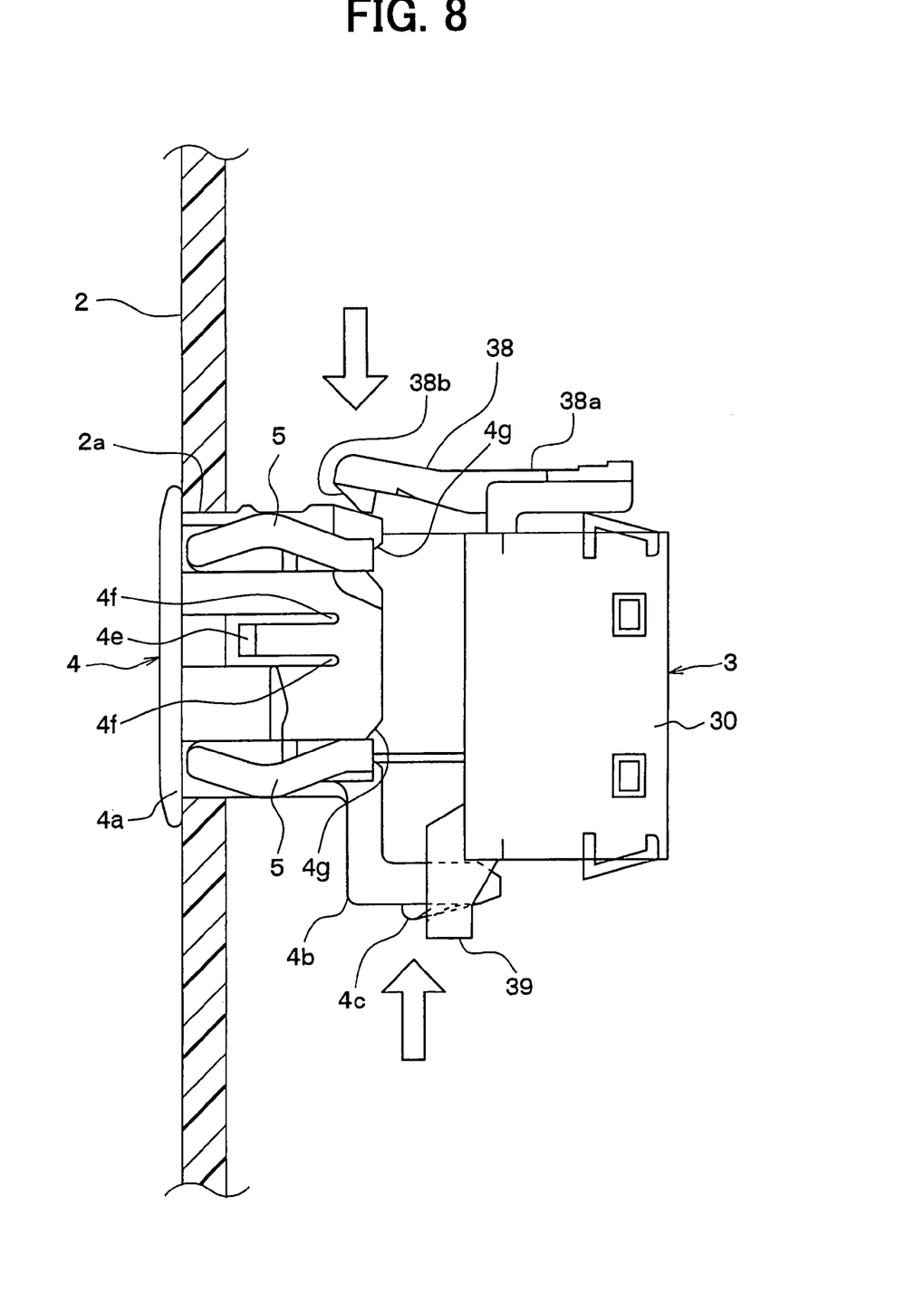
FIG. 8 is a partially sectional view showing a state of a midstream of the attachment of the ultrasonic sensor to the bumper according to the preferred embodiment.

Next, the attachment of the ultrasonic sensor 1 to the bumper 2 will be described. FIG. 7 shows the state before the ultrasonic sensor 1 is attached to the bumper 2. FIG. 8 shows the state of the midstream of the attachment of the ultrasonic sensor 1 to the bumper 2.

Figure 9:
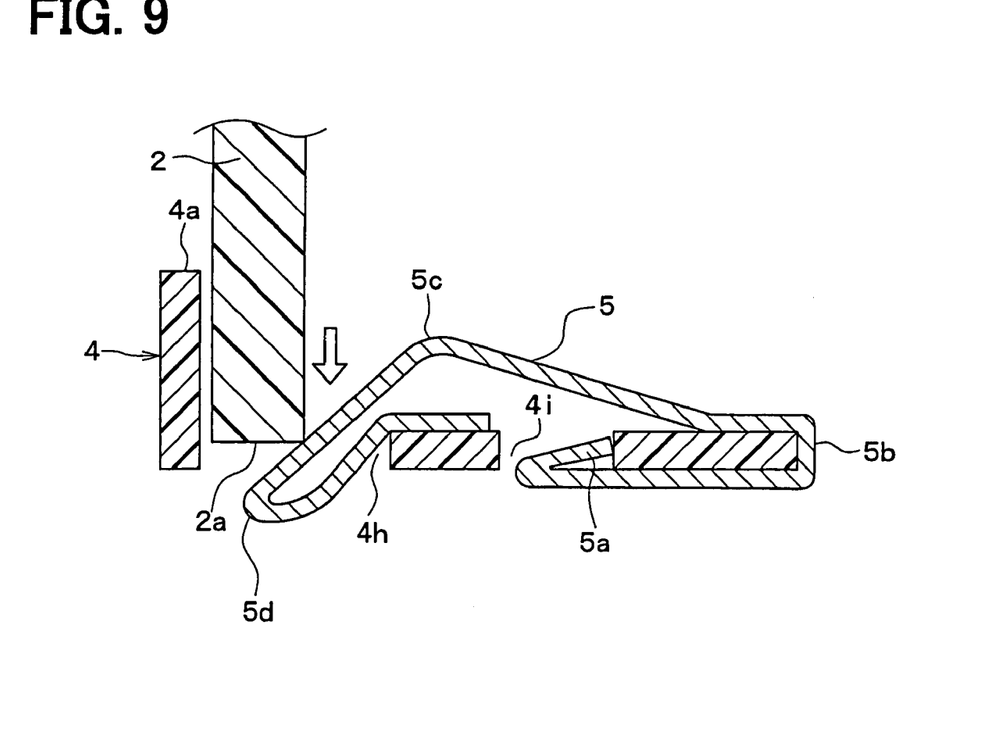
FIG. 9 is a partially sectional side view showing the cover member when being inserted into a hole portion of the bumper according to the preferred embodiment.

As shown in FIG. 7, at first, the cover member 4 is inserted into the hole portion 2a of the bumper 2 from the one side of the bumper 2 (that is, from the outer side of the bumper 2), until the detachment-restricting nail 4e enters into the inner side of the bumper 2. Thus, the opening end of the hole portion 2a contacts the slant portion of the convex portion 5c of the spring 5. FIG. 9 is an enlarged sectional view showing the state at this time.

As shown in FIG. 9, when the cover member 4 is inserted into the hole portion 2a, the spring 5 is elastically deformed to be bent by the opening end of the hole portion 2a of the bumper 2, and the loopback portion 5d which is the free end of the spring 5 enters into the through hole 4h to protrude from the inner wall of the hollow portion of the cover member 4.

Thereafter, as indicated by the arrow in FIG. 7, the opening portion 32 of the sensor body 3 and the ultrasonic sensor 10 are inserted into the hollow portion of the cover member 4 from the inner side (i.e., opposite side to flange 4a with respect to bumper 2) of the bumper 2. FIG. 10 is a partially enlarged sectional view showing the state when the opening portion 32 of the sensor body 3 and the ultrasonic sensor 10 are inserting into the hollow portion of the cover member 4.

As shown in FIGS. 8 and 10, the tip portion of the snap fit 4b enters into the hole of the receiving portion 39, and the nail portion 4c surrounded by the slit 4j contacts the inner wall of the receiving portion 39 to be elastically deformed. Thus, the snap fit 4b is inserted in the receiving portion 39. Thereafter, the part of the nail portion 4c which has been elastically deformed recovers, so that the nail portion 4c and the receiving portion 39 are engaged with each other to have the state shown in FIG. 1. Thus, the attachment is finished.

In this case, because the slit 4j having the ⊐-like shape to surround the nail portion 4c, the nail portion 4c can be readily elastically deformed with the part of the nail portion 4c of the front side with respect to the insertion direction (of nail portion 4c into receiving portion 39) as the fulcrum P1 and with the tip point of the nail portion 4c as the exertion point P2 of the force applied to the cover member 4, as shown in FIG. 10.

Thus, the fulcrum P1 and the exertion point P2 are respectively positioned at the two ends of the nail portion 4c. Because the distance between the fulcrum P1 and the exertion point P2 is set long, the nail portion 4c will have a smaller toppling angle when being elastically deformed, as compared with the case where the distance is set short. Accordingly, the rotation locus of the nail portion 4c can be decreased, so that the snap fit 4b can be firmly fixed to the receiving portion 39. Therefore, the sensor body 3 and the cover member 4 can be restricted from becoming wobbly.

Furthermore, when the shape of the nail portion 4c recovers, the inner wall surface of the receiving portion 39 and the wall surface of the tip portion of the snap fit 4b contact each other with little gap. Therefore, the snap fit 4b is firmly fixed by the receiving portion 39, so that the sensor body 3 and the cover member 4 can be restricted from becoming wobbly.

Moreover, as shown in FIGS. 8 and 10, the nail portion 38b of the lance 38 contacts the outer wall surface of the hollow portion of the cover member 4, and the rod portion 38a is elastically deformed with the tip point of the nail portion 38b as the exertion point P3 (of force applied to the cover member 4) and with the position of the base of the rod portion 38a of the lance 38 as the fulcrum P4. Then, the nail portion 38b enters into the engagement hole 4d, so that the part having being elastically deformed recovers and the lance 38 is engaged with the engagement hole 4d.

Forces with directions indicated by the arrows in FIG. 8 are exerted to the cover member 4, due to the engagement between the snap fit 4b and the receiving portion 39 and the engagement between the lance 38 and the engagement hole 4d of the cover member 4.

That is, about the engagement between the snap fit 4b and the receiving portion 39, because the nail portion 4c arranged at the snap fit 4b is pressed by the inner wall of the receiving portion 39, the force facing the axis direction of the hollow portion of the cover member 4 is applied to the snap fit 4b. That is, the force facing the upper side in FIG. 8 is applied to the cover member 4 to press the cover member 4.

Moreover, about the engagement between the lance 38 and the engagement hole 4d, the elastic reaction force (of the lance 38) which faces the axis direction of the hollow portion of the cover member 4 is applied to the cover member 4. That is, the force facing the lower side in FIG. 8 is applied to the cover member 4 to press the cover member 4. Therefore, the forces which are applied to the cover member 4 respectively face opposite directions, to be substantially countervailed. Thus, when the sensor body 3 is fixed to the cover member 4, the cover member 4 can be restricted from slanting.

Figure 11:
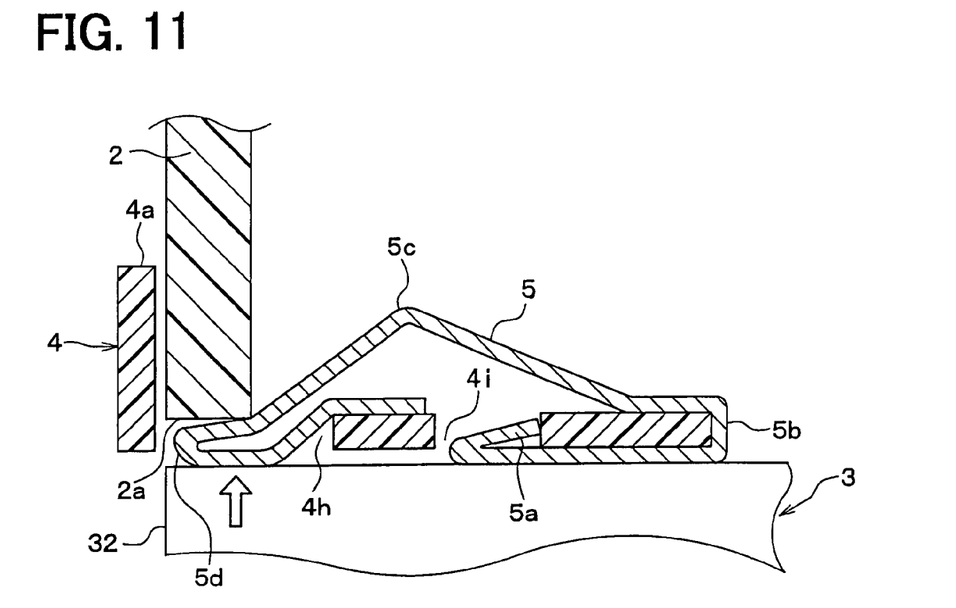
FIG. 11 is a partially sectional side view showing a state when the opening portion of the sensor body has been inserted into the hollow portion of the cover member according to the preferred embodiment.

Furthermore, the outer surface of the opening portion 32 of the case 30 contacts the part of the free end of the spring 5 which enters into the through hole 4h of the cover member 4 to protrude to the inner wall surface of the hollow portion of the cover member 4. FIG. 11 is a partially enlarged view showing this state.

As shown in FIG. 11, because the free end of the spring 5 contacts the outer surface of the opening portion 32, the spring 5 is pushed back in the expanding direction thereof in the diameter direction of the hollow portion of the cover member 4. Therefore, both of the bumper 2 and the outer surface of the opening portion 32 of the sensor body 3 contact the free end of the spring 5. In this case, an elastic force of the spring 5 is applied to the bumper 2 in the expanding direction thereof in the diameter direction of the cover member 4, at the free end of the spring 5. An elastic force of the spring 5 is applied to the opening portion 32 of the sensor body 3 in the shrinking direction thereof in the diameter direction of the cover member 4, at the free end of the spring 5.

That is, the free end of the spring 5 is elastically deformed to be compressed between the outer surface of the opening portion 32 and the wall surface of the hole portion 2a of the bumper 2. The sensor body 3 and the cover member 4 are fixed with respect to the wall surface of the hole portion 2a due to the elastic reaction force with the compression deformation.

According to this embodiment, the sensor body 3 is fixed to the bumper 2 through the cover member 4. In this case, the cover member 4 can be firmly fixed to the bumper 2, and the sensor body 3 can be firmly fixed to the cover member 4. Therefore, the ultrasonic sensor 1 can be firmly fixed to the bumper 2.

As described above, the sensor body 3 and the cover member 4 are respectively provided with the receiving portion 39 (third engagement portion) and the snap fit 4b (first engagement portion), and respectively provided with the lance 38 (fourth engagement portion) and the hole portion 4d (second engagement portion). The lance 38 and the engagement hole 4d are arranged at an opposite side of the hollow portion of the cover member 4, to the snap fit 4b and the receiving portion 39. Thus, the forces generated by the engagement portions are applied to the cover member 4 respectively in the opposite directions, when the sensor body 3 is fixed with respect to the cover member 4. Therefore, the cover member 4 can be restricted from slanting when the sensor body 3 is fixed to the cover member 4.

Other Embodiments

Although the present invention has been fully described in connection with the preferred embodiments thereof with reference to the accompanying drawings, it is to be noted that various changes and modifications will become apparent to those skilled in the art.

For example, in the above-described embodiment, the snap fit 4b, the engagement hole 4d, the receiving portion 39 and the lance 38 are provided as the engagement portions. However, the engagement portions are not limited to what are described above.

In the above-described embodiment, both the force generated by the engagement between the first engagement portion and the third engagement portion and the force generated by the engagement between the second engagement portion and the fourth engagement portion face the axial direction of the cylindrical direction of the cover member 4. However, the forces which substantially countervail each other can be also arranged to face a direction deviating from the axial direction.

Moreover, the cover member 4 and the part of the sensor body 3 which is inserted in the hollow portion of the cover member 4 can also have a shape other than the substantially circular shape. For example, the cover member 4 can have an oval cylinder shape, or a polygonal cylinder shape. The part of the sensor body 3 which is inserted into the hollow portion of the cover member 4 can have a shape (e.g., oval cylinder shape, or polygonal cylinder shape) corresponding to that of the hollow portion of the cover member 4.

Furthermore, in the above-described embodiment, the case where the ultrasonic sensor 1 is fixed by to the bumper 2 as the fixing member is described. However, the present invention can be also suitably used in the case where the ultrasonic sensor 1 is fixed to a vehicle component other than the bumper 2.

Such changes and modifications are to be understood as being in the scope of the present invention as defined by the appended claims.

What is claimed is:

1. An ultrasonic sensor, comprising:
a cover member having a hollow portion which defines therein a space and has an opening at one end thereof; and
a sensor body having an ultrasonic transducer, an insertion part of the sensor body which includes the ultrasonic transducer being inserted in the hollow portion from the opening of the cover member, wherein:
the insertion part of the sensor body is inserted in the hollow portion of the cover member from one side of a base after the cover member is inserted through a hole portion of the base from an other side of the base, so that the sensor body is attached to the base through the cover member,
the one side and the other side of the base being opposite to each other;
the cover member has a first engagement portion and a second engagement portion which are positioned to be opposite to each other with respect to the hollow portion of the cover member;
the sensor body has a third engagement portion which is engaged with the first engagement portion, and a fourth engagement portion which is engaged with the second engagement portion; and
the first engagement portion, the second engagement portion, the third engagement portion and the fourth engagement portion are arranged, in such a manner that a force applied to the cover member due to an engagement between the first engagement portion and the third engagement portion has a direction opposite to that of a force applied to the cover member due to an engagement between the second engagement portion and the fourth engagement portion when the sensor body is attached to the cover member.

2. The ultrasonic sensor according to claim 1, wherein:
the first engagement portion is a snap fit, which protrudes from an outer surface of the hollow portion of the cover member and has a nail portion protruding from a tip thereof;
the third engagement portion is a receiving portion which is arranged at the sensor body and has a substantial frame shape to construct a hole in which the nail portion is fitted; and
when the sensor body is attached to the cover member, the nail portion is pressed against an inner wall of the receiving portion so that a force facing a substantial axial direction of the hollow portion of the cover member is applied to the snap fit.

3. The ultrasonic sensor according to claim 2, wherein the snap fit has a slit which surrounds the nail portion.

4. The ultrasonic sensor according to claim 3, wherein:
the slit surrounds two opposite sides of the nail portion, and a rear side of the nail portion with respect to an insertion direction of the tip of the snap fit into the hole of the receiving portion; and
when the tip of the snap fit is inserted into the hole of the receiving portion, the nail portion is elastically deformed in such a manner that a part of the nail portion of a front side in the insertion direction constructs a fulcrum and a tip of the nail portion constructs an exertion point.

5. The ultrasonic sensor according to claim 1, wherein:
the second engagement portion is a hole portion which is arranged at the hollow portion of the cover member;
the fourth engagement portion is a lance which protrudes from the sensor body and has a nail portion fitted in the hole portion; and
when the sensor body is attached to the cover member, the hollow portion of the cover member is pressed by the nail portion so that the a force facing a substantial axial direction of the hollow portion is applied to the cover member.

6. The ultrasonic sensor according to claim 1, wherein the base is a vehicle component.

* * * * *